(12) United States Patent
Molnar-Hammond et al.

(10) Patent No.: US 11,129,662 B2
(45) Date of Patent: *Sep. 28, 2021

(54) ABLATION PROBE WITH DEPLOYABLE SENSORS

(71) Applicant: CPSI HOLDINGS LLC, Owego, NY (US)

(72) Inventors: Marie Molnar-Hammond, Chester Springs, PA (US); John M. Baust, Candor, NY (US)

(73) Assignee: CPSI Holdings LLC, Owego, NY (US)

( * ) Notice: Subject to any disclaimer, the term of this patent is extended or adjusted under 35 U.S.C. 154(b) by 429 days.

This patent is subject to a terminal disclaimer.

(21) Appl. No.: 16/030,933

(22) Filed: Jul. 10, 2018

(65) Prior Publication Data

US 2018/0317994 A1 Nov. 8, 2018

Related U.S. Application Data

(63) Continuation of application No. 14/190,806, filed on Feb. 26, 2014, now Pat. No. 10,039,586.

(60) Provisional application No. 61/769,280, filed on Feb. 26, 2013.

(51) Int. Cl.
| | |
|---|---|
| *A61B 18/02* | (2006.01) |
| *A61B 18/14* | (2006.01) |
| *A61B 17/00* | (2006.01) |
| *A61B 18/00* | (2006.01) |

(52) U.S. Cl.
CPC ......... *A61B 18/02* (2013.01); *A61B 18/1477* (2013.01); *A61B 2017/00106* (2013.01); *A61B 2018/00577* (2013.01); *A61B 2018/00773* (2013.01); *A61B 2018/00797* (2013.01); *A61B 2018/00875* (2013.01); *A61B 2018/0262* (2013.01); *A61B 2018/0293* (2013.01)

(58) Field of Classification Search
CPC ............... A61B 18/02; A61B 18/12; A61B 2018/00011; A61B 2018/00017; A61B 2018/00023; A61B 2018/00041; A61B 2018/0212; A61B 2018/0262; A61B 2018/0293

See application file for complete search history.

(56) References Cited

U.S. PATENT DOCUMENTS

| | | | | |
|---|---|---|---|---|
| 5,403,309 A | * | 4/1995 | Coleman | A61B 17/42 604/113 |
| 5,868,735 A | * | 2/1999 | Lafontaine | A61B 18/02 606/21 |
| 6,330,478 B1 | | 12/2001 | Lee et al. | |

(Continued)

*Primary Examiner* — Ronald Hupczey, Jr.
(74) *Attorney, Agent, or Firm* — Hoffman Warnick LLC

(57) ABSTRACT

The present disclosure relates to a thermal ablation probe device that integrates deployable sensors with a freezing probe or heating probe for use in ablating tissues. The ablation probe includes a longitudinal body including a thermal ablation energy source which may be, e.g., a cryosource or a heat source. The longitudinal body has a proximal end and a distal end terminating at a probe tip; and at least one deployable assembly disposed within the longitudinal body. The deployable assembly includes a flexible and substantially rigid deployment member, and at least one sensor affixed to a distal end of the deployment member. The ablation probe further includes a control mechanism for controlling deployment and retraction of the deployable assembly.

12 Claims, 10 Drawing Sheets

316

(56) References Cited

U.S. PATENT DOCUMENTS

| | | | |
|---|---|---|---|
| 6,355,029 B1* | 3/2002 | Joye | A61B 18/02 606/21 |
| 6,514,249 B1 | 2/2003 | Maguire et al. | |
| 6,709,431 B2* | 3/2004 | Lafontaine | A61B 18/02 606/20 |
| 6,726,677 B1 | 4/2004 | Flaherty et al. | |
| 7,473,250 B2 | 1/2009 | Makin et al. | |
| 8,348,855 B2* | 1/2013 | Hillely | G01K 1/026 600/549 |
| 8,419,613 B2 | 4/2013 | Saadat et al. | |
| 10,039,586 B2* | 8/2018 | Molnar-Hammond | A61B 18/1477 |
| 2002/0049436 A1 | 4/2002 | Zvuloni et al. | |
| 2002/0151880 A1* | 10/2002 | Lafontaine | A61B 18/02 606/21 |

* cited by examiner

ABLATION PROBE WITH DEPLOYABLE SENSORS

CROSS REFERENCE TO RELATED APPLICATION

The present application is a continuation of U.S. application Ser. No. 14/190,806, filed Feb. 26, 2014, which claims the benefit of U.S. Provisional Application Ser. No. 61/769,280, filed Feb. 26, 2013. The entirety of each of the foregoing is incorporated herein as though fully set forth.

FIELD OF THE INVENTION

The present invention relates generally to the medical technology field and, in particular, to an ablation device and method for measuring tissue characteristics during thermal treatments.

BACKGROUND OF THE INVENTION

Tissue ablation can be performed to remove undesired tissue such as cancer cells, or may involve the modification of tissue without removal, such as to stop electrical signal propagation through tissue in patients with, e.g., a cardiac arrhythmia. Often the ablation is performed by passing energy, such as electrical energy, through one or more electrodes causing the tissue in contact with the electrodes to be heat ablated. Cryo-probes and cryo-catheters are also used to freeze the tissue during cryoablation. Cryoablation is used to treat various diseases and disorders including, for example, liver tumors, actinic keratoses, breast cancer, colorectal cancer, cervical intraepithelial neoplasia, prostate cancer, and atrial fibrillation. Cryosurgery creates an iceball that is easily visualized within a defined zone, but is difficult to control or monitor temperatures at the periphery. Other probes employ the use of energy sources including microwaves, lasers, and high intensity ultrasonic devices that mechanically destroy the tissue.

In thermal ablation, collecting information regarding the three-dimensional thermal profile of tissues in and around a treatment zone is extremely important. In view of the tissue temperature gradients that exist during hypothermia and hyperthermia treatments as a consequence of differences in blood flow and thermal conductivity of tissue, temperature monitoring is crucial at multiple sites in and around the treatment zone. Temperature gradients will be greatest at the boundaries of differential energy absorption, perfusion and conductivity, and thus, knowing the temperature throughout the targeted area including at the tumor margin or proliferating edge would be advantageous.

Typically, to measure probe temperature, thermosensors are placed inside a probe or on an outer surface of the probe to monitor temperature at the tip of the probe, also known as "tip temperature." Tip temperature is often defined as the temperature within the inside of the probe tip, on the outer surface of the ablation lumen, or at any point along the ablation zone of a device.

During cryoablation, once the probe is inserted into a body of tissue, the position of the probe and thermal sensors within the probe are fixed with respect to that tissue and cannot be moved or displaced so long as that tissue is frozen. The immobility of the thermal sensors within such a probe thus severely limit the ability of the probe to provide detailed and accurate thermal information regarding temperatures at a wide variety of positions within and around the iceball created by a cryoablation procedure. Furthermore, this temperature recording does not reflect the temperature of tissues at the periphery of the iceball near surrounding tissues. For example, to attain a designated temperature within a target tissue, the freeze area extends beyond the periphery of the target and into surrounding non-target tissue. In an argon-based system, this means a large portion of the damaged tissue is outside the target site. In a liquid nitrogen based system, colder isotherms are achieved throughout the iceball to increase cell death and control destruction of the targeted tissue, but over-freeze can damage surrounding non-target tissue.

To monitor tissue temperature surrounding a probe prior to, during, or following a procedure, separate thermal monitoring devices have been inserted adjacent or perpendicular to an ablation probe. Issues in positioning and placing the probes with thermal sensors, however, make temperature measurements throughout an entire ablative zone difficult if not impossible. Without effective temperature monitoring, heat ablation and cryoablation procedures are not able to effectively ablate all of the target tissue and avoid damage to surrounding healthy tissues. For example, cancerous tissue may be left behind where ablation is not achieved at the target site due to unknown temperatures within the tumor and within surrounding healthy tissues.

In one method of heat ablation, radio-frequency ablation (RFA) is delivered and monitored by use of temperature or impedance generators. Temperature-based generators allow probes to become heated at a preset value for a predetermined length of time. Temperatures above 50° C. are required for cell injury. Unfortunately, probe and tissue temperatures may not necessarily correlate. This affects cell destruction as heat sensitivity varies between normal tissue and diseased tissue. Further, blood vessels near a treatment zone serve as a heat sink and make it difficult to control and monitor the target temperature.

Impedance generators are another method of monitoring the ablation process. Typically, impedance levels higher than 200Ω are utilized. Comparison of impedance-monitored and temperature monitored RFA generators have indicated that equivalent ablation zones can be created. As charred tissue adheres to the probe surface, however, an artificial increase in impedance may result, thus limiting the ablation zone. Modifications in the generator and the probe have thus led to the development of 'wet' or 'cool' RFA. Cool saline irrigation disperses charred tissue, allowing more efficient conductive heat transfer.

As described, the common monitoring that defines effective ablation is the temperature at which the tissue is destroyed (ablated) via mechanisms of physical destruction, necrosis, and/or apoptosis. To achieve effective ablation throughout a target tissue, a desired temperature at or beyond the margin (edge) of a given area must be attained. Currently, accurate and effective monitoring of temperatures at precise locations is extremely difficult requiring the utilization and interpretation of data from independent temperature recording and visualization devices such as, e.g., ultrasound. This often results in improper or inaccurate placement of thermosensors which can result in incomplete or excessive tissue destruction during an ablation procedure. Further, the target tissue for ablation may be located where the placement of additional thermosensors or visualization is not possible, making it difficult to effectively monitor the ablation zone.

SUMMARY OF THE INVENTION

According to a first aspect, an ablation probe is provided for performing a thermal ablation procedure. The ablation probe includes a longitudinal body including a thermal ablation energy source, the longitudinal body having a proximal end and a distal end terminating at a probe tip; and at least one deployable assembly disposed within the longitudinal body. The deployable assembly includes a flexible and substantially rigid deployment member, and at least one sensor affixed to a distal end of the deployment member. The ablation probe further includes a control mechanism for controlling deployment in a distal direction and retraction in a proximal direction of the deployable assembly.

According to a second aspect of the invention, a method is provided for monitoring tissue characteristics during a thermal ablation procedure. The method includes inserting an ablation probe into a target tissue. The ablation probe includes a longitudinal body including a thermal ablation energy source, the longitudinal body having a proximal end and a distal end terminating at a probe tip; at least one deployable assembly disposed within the longitudinal body, and a control mechanism for controlling deployment and retraction of the deployable assembly. The deployable assembly further includes a flexible and substantially rigid deployment member, and at least one sensor affixed to a distal end of the deployment member. In any event, following insertion of the ablation probe into the target tissue, the deployable assembly is deployed into at least one of the target tissue and a non-target tissue; and a hyperthermic or hypothermic temperature gradient is initiated in the target tissue to create an ablation zone. The temperature gradient includes a change in temperature from the ablation probe radially outward to the non-target tissue. The method further includes monitoring at least one tissue characteristic in at least one of the target tissue or the non-target tissue during the ablation procedure.

These and other aspects, advantages and salient features of the invention will become apparent from the following detailed description, which, when taken in conjunction with the annexed drawings, disclose embodiments of the invention.

Figure 1:
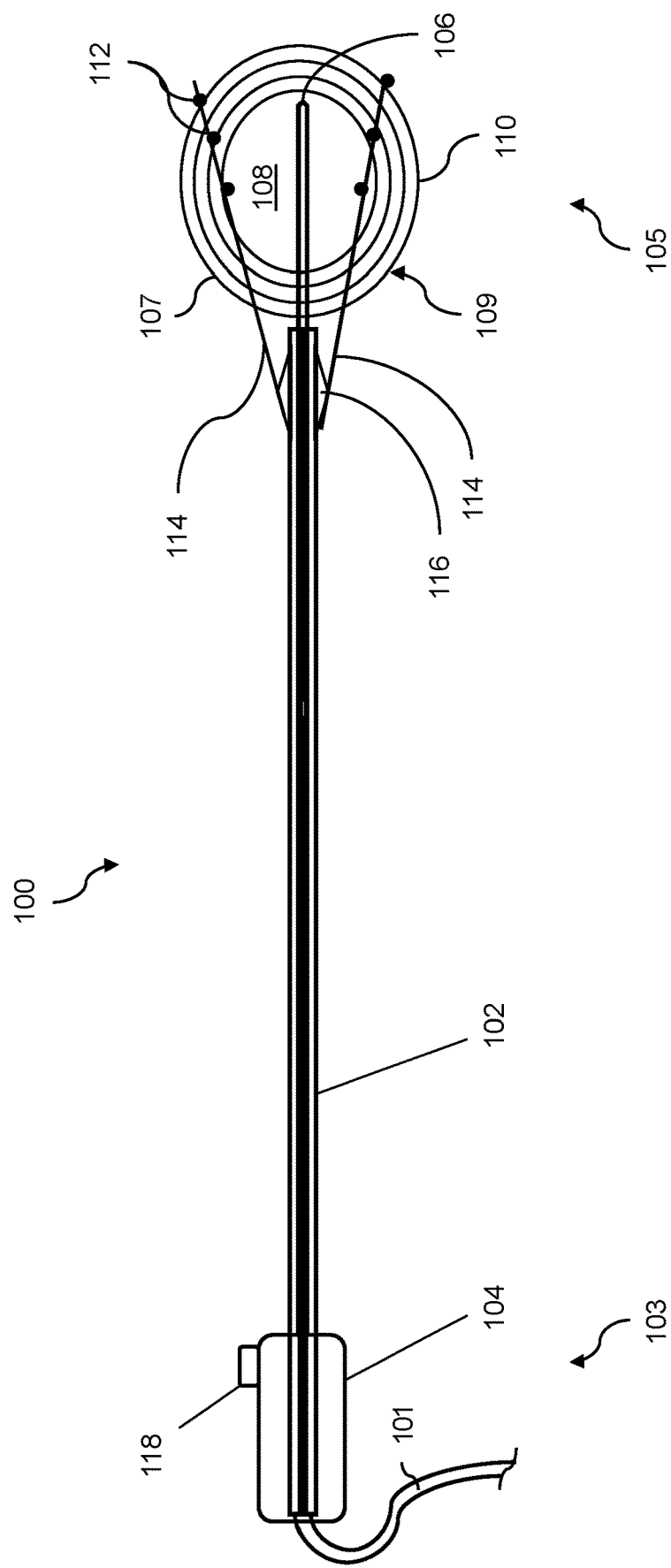
FIGS. 1-2 provide side views of ablation probes in accordance with embodiments of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

Turning to the drawings, FIGS. 1-10 provide various embodiments of an ablation probe device and method for using the same.

Figure 2:
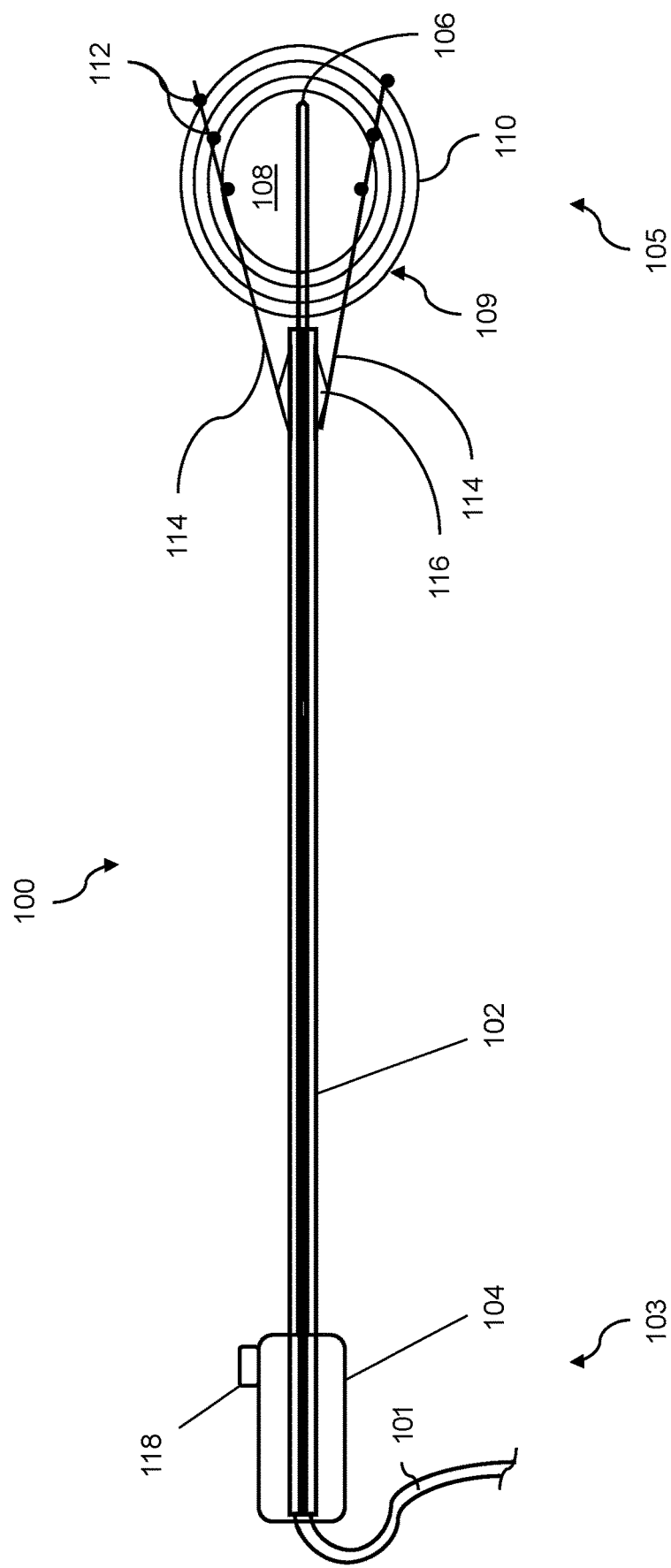

FIGS. 1-2 depict an ablation probe with integrated deployable sensors, hereinafter referred to as device 100. As shown in FIG. 1, device 100 includes a longitudinal body 102 with a proximal end 103 and a distal end 105. The longitudinal body 102 integrates a source of thermal energy 101 therein. As shown in, e.g., FIGS. 1 and 3, device 100 may be a cryoprobe, and the source of thermal energy 101 may include a supply line 120 (FIG. 3) for supplying, for example, nitrogen, argon, carbon dioxide, nitrous oxide, propane, an alcohol solution, or another cryosource as known in the art, either in a gas, liquid, critical, or supercritical state to probe tip 106. A return line 122 (FIG. 3) may further be provided for returning used cryosource fluid from probe tip 106. In some embodiments, return line 122 may be in the form of a tube, and may be arranged such that it concentrically surrounds supply tube 120. Return line 122 may itself be concentrically surrounded by an insulative lumen 124, which may further be surrounded by outer sheath 126 of the probe. With reference to FIG. 2, in various other embodiments, source of thermal energy 101 may include any other source of thermal energy known in the art, including, e.g., heat sources such as radio frequency (RF) energy, high intensity focused ultrasound (HiFU), thermoelectric resistive heat, lasers, helium gas, or other energy sources, either alone or in combination with a cryosource.

Referring back to FIG. 1, longitudinal body 102 may include a probe tip 106 disposed at distal end 105. During use of device 100, probe tip 106 may be placed at the target tissue site for performing ablation therapy. As further depicted in FIG. 1, in embodiments in which device 100 is a cryoablation device, operation of device 100 at the target tissue site may cause the formation of iceball 107 surrounding probe tip 106, with an ablation zone 108 disposed within iceball 107. Ablation zone 108 may include tissue at temperatures as low as, e.g., −196° C. or colder. In other procedures, ablation zone 108 may include tissue at temperatures in the range of, e.g., −20° C. to −40° C. or colder. Tissues in the range of, e.g., −20° C. to 0° C. may be included within iceball 107 but may be outside ablation zone 108. Iceball 107 may include a temperature gradient 109 extending radially outward from probe tip 106 and ablation zone 108. Along temperature gradient 109, colder temperatures may be found proximate to probe tip 106 and in ablation zone 108, becoming gradually warmer approaching periphery 110 of iceball 107. Periphery 110 of iceball 107 may be about 0° C. It is noted, however, that the thermal transition point that defines the outer edge of the ablation zone and the periphery varies based on the type of tissue targeted. The temperatures provided herein are merely intended to be exemplary.

Similarly, in embodiments in which device 100 is a hyperthermic ablation device, such as shown in FIG. 2, operation of device 100 at the target tissue site heats the target tissue to a point at which lethality is achieved in the tissue surrounding probe tip 106. Probe tip 106 may reach temperatures of upwards of 100° C., and ablation zone 108 may include tissue heated to temperatures exceeding 40° C., or more particularly in the range of, e.g., 42° C. to 45° C., or 42° C. to 60° C. or higher. Ablation zone 108 may be surrounded by temperature gradient 109 extending radially outward from probe tip 106 and ablation zone 108, to a periphery 110 of the lesion. Temperatures along temperature gradient 109 may be in the range of, e.g., 42° C. just radially outward of ablation zone 108 to about 37° C. near periphery 110. As discussed above relative to FIG. 1, it is noted that the temperatures provided herein are merely intended to be exemplary.

As shown in FIGS. 1-2, device 100 may further include a probe handle 104 disposed at proximal end 103 of longitudinal body 102. In some embodiments, probe handle 104 may be integrally formed with longitudinal body 102. Probe handle 104 may include control mechanism 118 for operating device 100. In some embodiments, control mechanism 118 may be a push button for controlling insertion of deployable assemblies 114 and sensors 112 (discussed further below) into a designated target tissue. In other embodiments, control mechanism 118 may include a screw-like mechanism, with the driving force applied manually, or via motor, piston, pneumatics, or other means of causing physical movement of sensors 112 and deployable assembly 114 into the tissue.

As further shown in FIGS. 1-2, a plurality of sensors 112 are arranged on a deployable assembly 114 for positioning sensors 112 in and along the ablation zone 108. In some embodiments, deployable assembly 114 may include a wire or wires encased in a stiff outer covering, which may be plastic, metal, or another material. The stiff outer covering may provide added rigidity to deployable assembly 114 for guiding the trajectory of sensors 112 into a target tissue. In the embodiment shown in FIG. 1, two deployable assemblies 114 are illustrated, although in various other embodiments, one, two, or more than two deployable assemblies 114 may be included in device 100. It is noted that each deployable assembly 114 may be independently operated, both in binary terms of deployment and retraction, and in degree, i.e., deployable assemblies may be deployed at different percentages of their fully deployed extensions. In one example, a first deployable assembly 114 may be deployed fully, i.e., 100% extended, while a second deployable assembly 114 may be deployed to only 50% of its full extension.

In various embodiments, sensors 112 on each deployable assembly 114 may monitor one or more tissue characteristics, such as temperature, pressure, electrical impedance, electrical conduction, blood perfusion, thermal conductivity, thermal diffusivity, sound propagation velocity or another desired metric during the ablation process in both ablation zone 108 and the surrounding non-target tissues so that collateral damage to the surrounding areas is reduced. In various embodiments, sensors 112 may specifically be temperature sensors, and may include one or a combination of thermal couples, resistance temperature detectors (RTDs), or solid state temperature devices. Further, sensors may include electrical conduction monitors, tissue impedance rings or point sensors, or acoustic, infrared or other such sensors capable of monitoring the state, functionality, electrical characteristics and temperature within a target tissue prior to during and or following a procedure. In other embodiments, sensors 112 may record and/or transmit measurements to a user device.

As noted, deployable assembly 114 and its respective sensors 112 may be used to monitor temperature and other metrics during an ablation procedure at multiple points. During use of device 100, deployable assembly 114 can be positioned at various points within the ablation zone 108 along and/or across the temperature gradient 109 to periphery 110.

Deployable assembly 114 may be strategically positioned during a procedure to align sensors 112 with isotherms created during the ablation process. In still further embodiments, deployable assembly 114 and/or probe tip 106 may include integrated heating elements to allow for the "thawing" of tissue around probe tip 106 to facilitate quicker tissue thawing and probe removal following completion of a cryoablation procedure.

In various embodiments, deflection wedges 116 may be provided on a radially outer surface or within the shaft of longitudinal body 102 of device 100. Deflection wedges may be located near the distal end 105 of longitudinal body 102, just proximal of ablation zone 108. Deflection wedges 116 may be configured as described further below to direct deployable assembly 114 carrying sensors 112 into the target tissue at a particular angle relative to the probe surface. The specific angles may be calibrated to the desired zones or to locations within a target tissue at a desired distance from the probe tip 106 following probe insertion into a target tissue.

Figure 3:
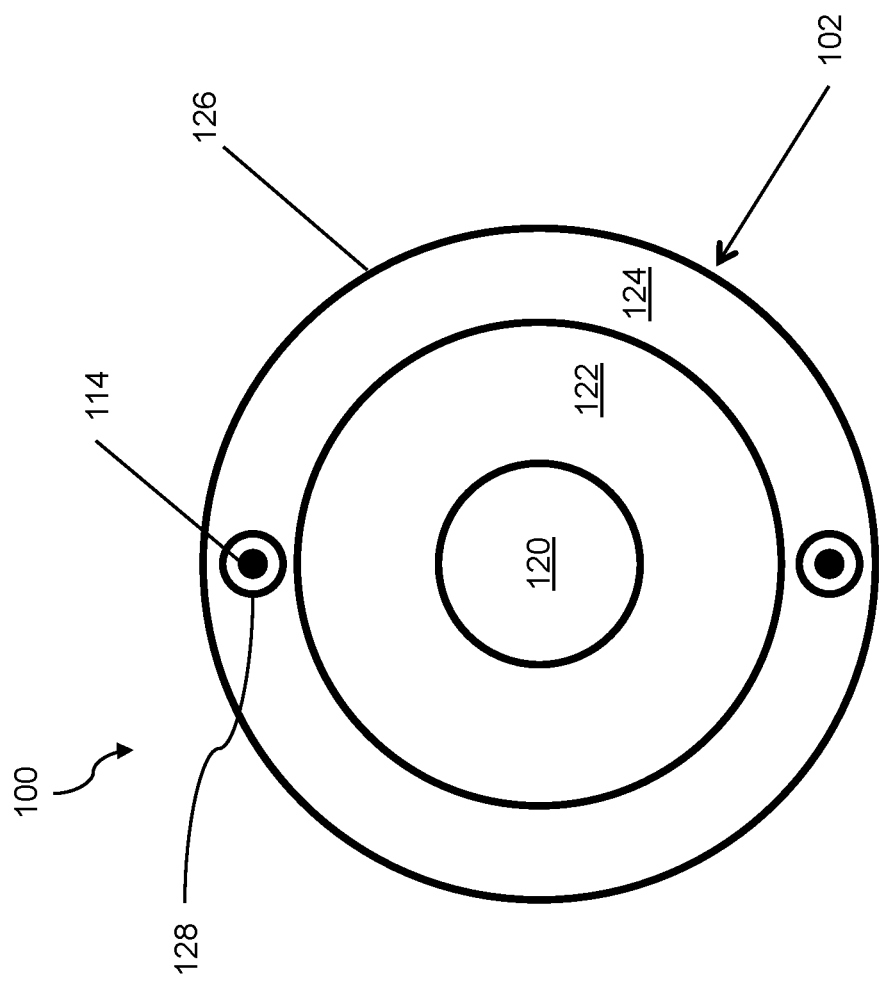
FIG. 3 is a cross sectional view of an ablation probe in accordance with an embodiment of the invention.
Figure 4:
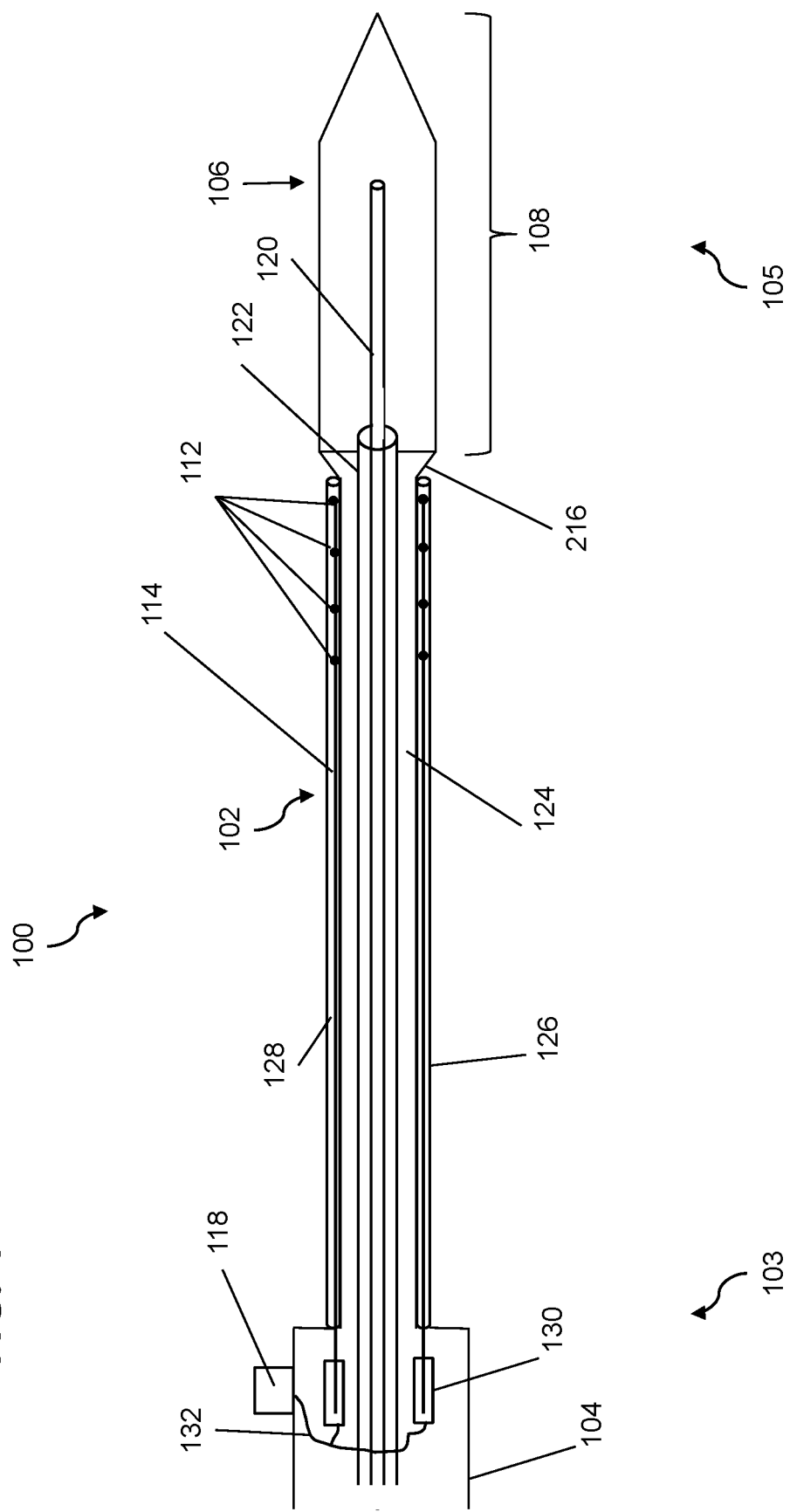
FIGS. 4 and 5 are longitudinal cross sectional views of an ablation probe, with sensors retracted and deployed respectively, in accordance with an embodiment of the invention.
Figure 5:
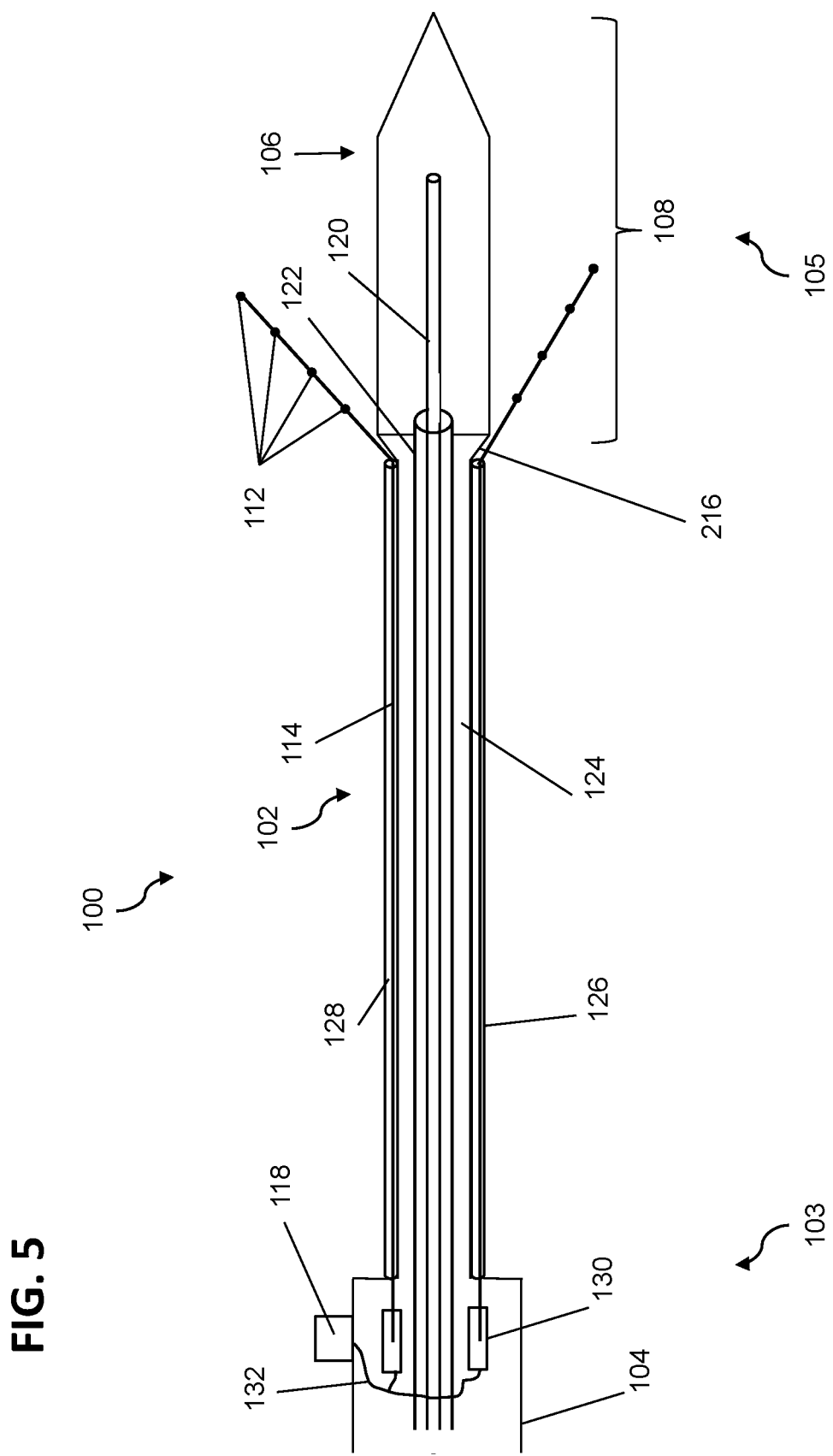

With reference to FIGS. 3-5, an embodiment of device 100 is illustrated in which device 100 is a cryoablation device including longitudinal body 102 (FIGS. 4-5). As shown in FIG. 3, longitudinal body 102 may include a supply tube 120 for supplying a fluid thermal energy source to device 100, and a return tube 122 for returning the used fluid thermal energy source. Return tube 122 may concentrically surround supply tube 120, and return tube 122 may be concentrically surrounded by an insulative lumen 124. Insulative lumen 124 may further be surrounded by probe outer sheath 126.

At least one integrated guide channel 128 may be provided within insulative lumen 124. In some embodiments, two integrated guide channels 128 may be provided, and may be disposed approximately 180° around lumen 124 from one another. Integrated guide channels 128 may extend along the full axial length of longitudinal body 102, as shown in FIGS. 4-5. Deployable assembly 114, including sensors 112, may be disposed within integrated guide channel 128 between return tube 122 and outer probe sheath 126. As shown in FIGS. 4-5, at proximal end 103, deployable assembly 114 may be coupled to insertion mechanism 130, which may be coupled to control wiring 132, which may in turn be coupled to control mechanism 118. As described above, control mechanism 118 may be, e.g., a push button mechanism.

In the retracted position, as shown in FIG. 4, each deployable assembly 114 may be contained substantially within an integrated guide channel 128. Upon deployment, shown in FIG. 5, deployable assembly 114 may be extended distally such that sensors 112 of deployable assembly 114 are inserted into ablation zone 108.

With continued reference to FIGS. 4-5, distal end 105 of longitudinal body 102 may include at least one internal deflection wedge 216 for guiding the position of deployment assembly 114 about probe tip 106 and into ablation zone 108. In some embodiments, two internal deflection wedges 216 may be provided. Internal deflection wedges 216 may either be an independent member or may be integrated as a portion of distal end 105 of probe tip 106. Internal deflection wedges 216 include an angled face that extends distally and radially outward, guiding each deployable assembly 114 distally and radially outward as it is deployed.

Figure 6:
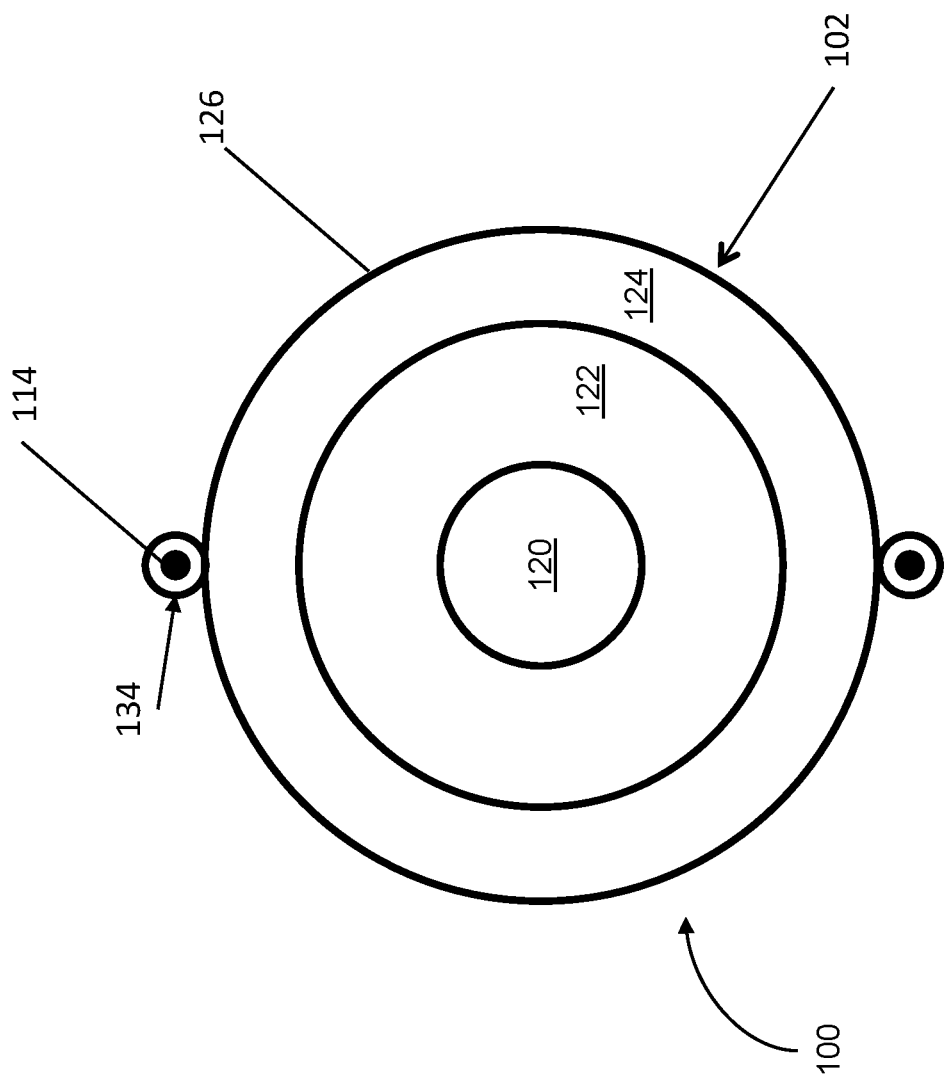
FIG. 6 is a cross sectional view of an ablation probe in accordance with an embodiment of the invention.
Figure 7:
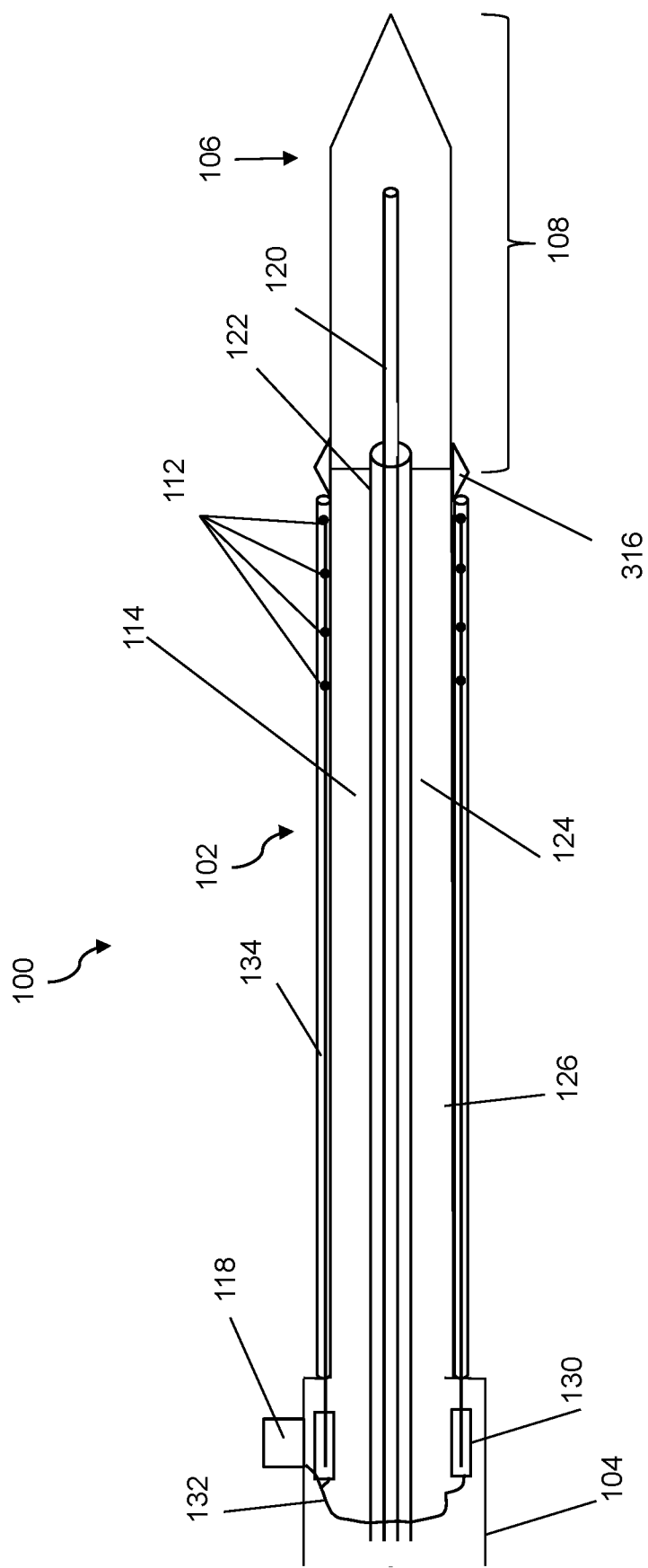
FIGS. 7 and 8 are longitudinal cross sectional views of an ablation probe, with sensors retracted and deployed respectively, in accordance with an embodiment of the invention.
Figure 8:
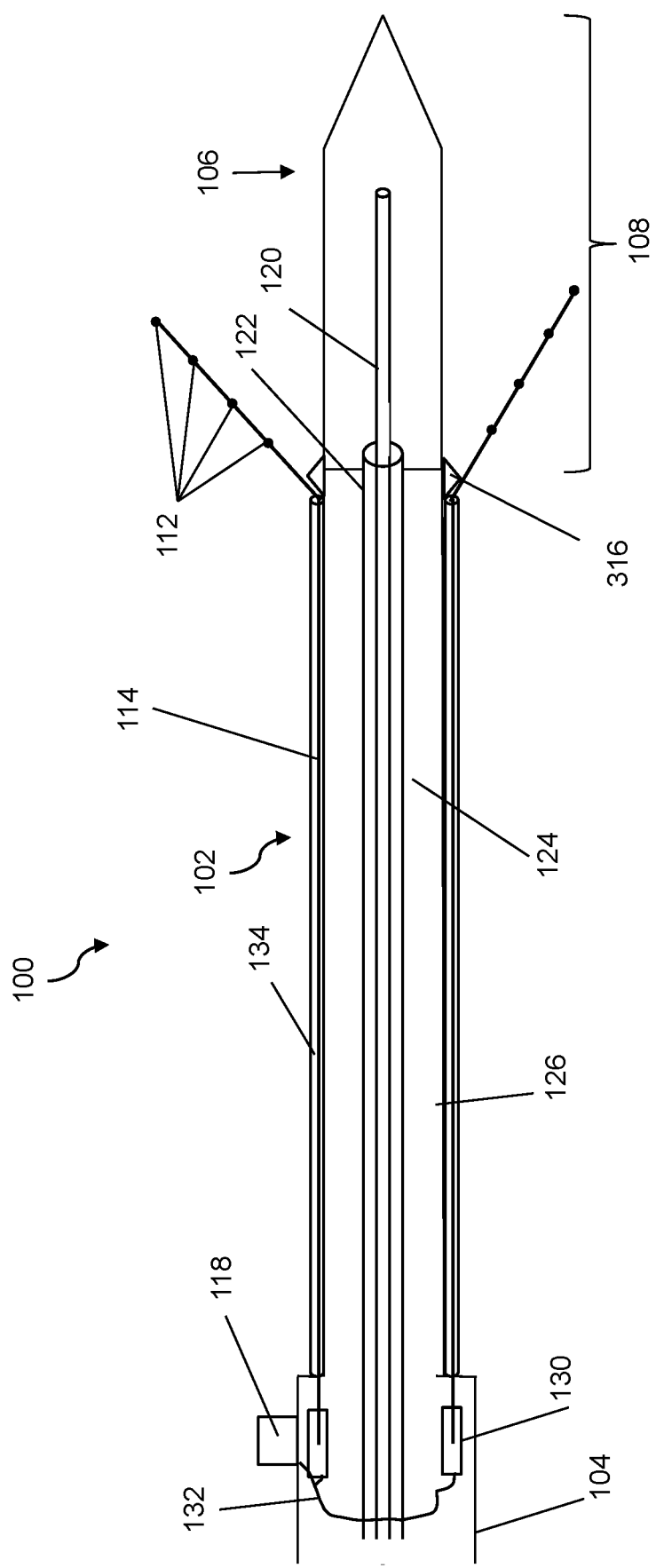

With reference to FIGS. 6-8, a further embodiment of device 100 is illustrated. As described above relative to FIGS. 3-5, the device 100 shown in FIGS. 6-8 may be a cryoablation device including longitudinal body 102 having a supply tube 120, return tube 122, insulative lumen 124, and an outer sheath 126 arranged in a similar fashion. As best shown in FIG. 6, an outer guide channel 134 may be provided on a radially outer surface of outer probe sheath 126. In some embodiments, two outer guide channels 134 may be provided, and may be disposed approximately 180° around outer probe sheath 126 from one another. Guide channels 134 may extend along the full axial length of longitudinal body 102, and provide a conduit for deployable assemblies 114 to extend from proximal end 103 to distal end 105.

In the retracted position, as shown in FIG. 7, deployable assembly 114, including sensors 112, may be disposed within outer guide channel 134, radially outward of outer probe sheath 126. At proximal end 103, deployable assembly 114 may be coupled to insertion mechanism 130, which may be coupled to control wiring 132, which may in turn be coupled to control mechanism 118, similar to the embodiment of FIGS. 3-5.

Upon deployment, shown in FIG. 8, deployable assembly 114 may be extended distally such that sensors 112 of each deployable assembly 114 are inserted into ablation zone 108. Distal end 105 of longitudinal body 102 may include at least one surface mounted deflection wedge 316 for guiding the position of each deployment assembly 114 about probe tip 106 and into ablation zone 108. In some embodiments, two surface mounted deflection wedges 316 may be provided.

Surface mounted deflection wedges 316 may be substantially triangular in cross sectional profile, but may also have any other profile shape such that they include a face extending radially outward and distally from a distal end 105 of longitudinal body 102. This face serves to guide each deployable assembly 114 distally and radially outward as it is deployed. Surface mounted wedges 316 may further include a base that is mounted or affixed to, or integrally formed with outer probe sheath 126. Surface mounted deflection wedges 316 may either be independent members affixed to longitudinal body 102 or may be integrated as a portion of distal end 105 of probe tip 106.

Figure 9:
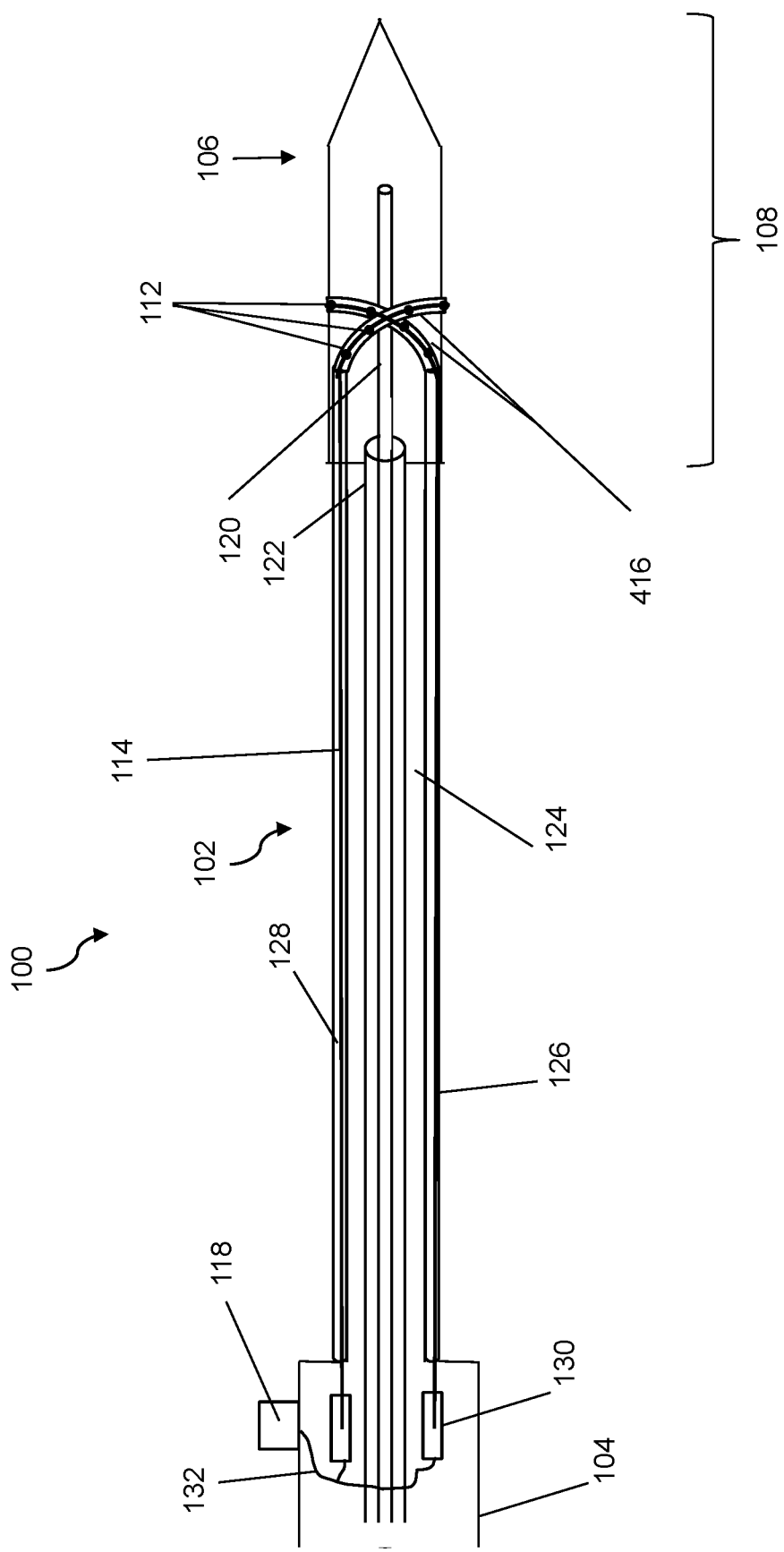
FIGS. 9 and 10 are longitudinal cross sectional views of an ablation probe, with sensors retracted and deployed respectively, in accordance with an embodiment of the invention.
Figure 10:
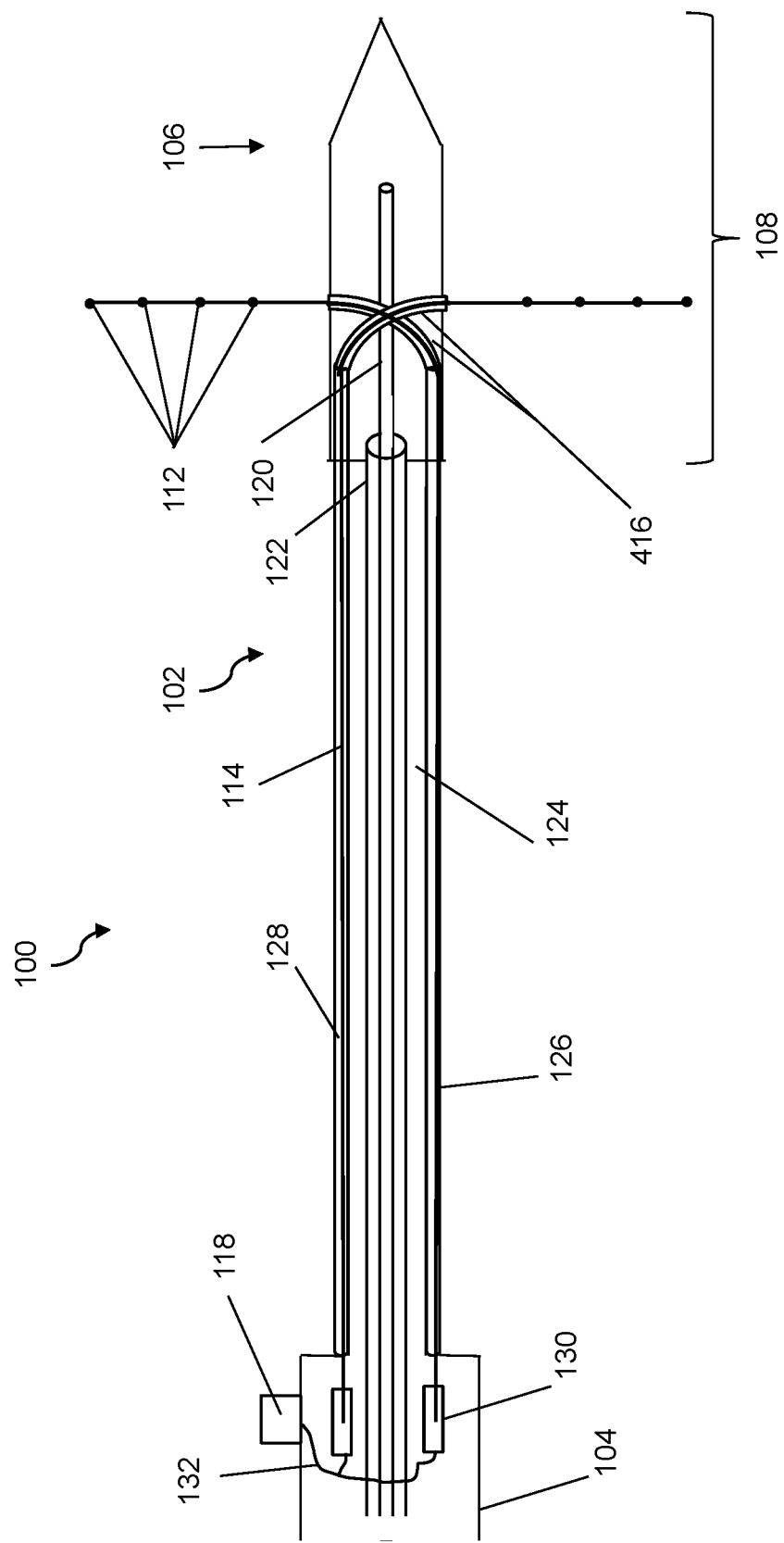

With reference to FIGS. 9-10, another possible embodiment of device 100 is illustrated. Similar to the preceding embodiments, device 100 as shown in FIGS. 9-10 may be a cryoablation device including longitudinal body 102 having a supply tube 120, return tube 122, insulative lumen 124, and an outer sheath 126 arranged in a similar fashion.

At least one integrated guide channel 128 may be provided within insulative lumen 124. In some embodiments, two integrated guide channels 128 may be provided, and may be disposed approximately 180° around lumen 124 from one another. Integrated guide channels 128 may extend along the full axial length of longitudinal body 102 as described relative to FIGS. 3-5.

In the retracted position, as shown in FIG. 9, deployable assembly 114, including sensors 112, may be disposed within integrated guide channel 128 between return tube 122 and outer probe sheath 126. At proximal end 103, deployable assembly 114 may be coupled to insertion mechanism 130, which may be coupled to control wiring 132, which may in turn be coupled to control mechanism 118 as described previously.

At distal end 105 of longitudinal body 102, an internal deflection tube 416 may be provided, at a ratio of one internal deflection tube 416 for each integrated guide channel 128. Internal deflection tube 416 may be positioned such that a proximal end of internal deflection tube 416 abuts the distal end of integrated guide channel 128, such that deployable assembly 114 advances distally from internal guide channel 128 into and through internal deflection tube 416 as it is deployed into ablation zone 108. Internal deflection tube 416 may guide deployment assembly 114 into position about probe tip 106. In particular, internal deflection tube 416 may be shaped to direct deployable assembly 114 in a curve that may be approximately 90° (or other appropriate angle, either more obtuse or more acute) from its trajectory along integrated guide channel 128. In particular, internal deflection tube 416 may deflect deployable assembly 114 such that a distal end of deployable assembly 114 bends and curves/ extends across a cross section of longitudinal body 102 in a retracted position, and in a deployed position, extends radially outward at an angle relative to longitudinal body 102. For example, in the embodiment depicted in FIG. 10, in the deployed position, deployable assembly 114 extends substantially perpendicularly to longitudinal body 102, although an approximate 90° angle is merely exemplary. In some embodiments, sensors 112 of each deployable assembly 114 may be positioned within internal deflection tube 416 in the retracted position, prior to their deployment radially outward of longitudinal body 102.

With reference to all of the preceding embodiments, independent or integrated internal or surface mounted wedge 216, 316 or deflection tube 416 configurations may be compatible with any of the device 100 configurations described above. Further, the angle of the wedge 216, 316 or tube 416 can vary based on the type of device 100, its use and configuration. In one configuration, the wedge 216, 316 angle or tube 416 angle may be set to allow for a position of sensors 112 to correspond to regions of critical interest when fully deployed. For instance, in one configuration the wedge 216, 316 angle or tube 416 angle is set such that sensors 112 are positioned upon deployment to locations where the desired −40° C., −20° C., and 0° C. isotherms should be achieved by the end of the ablation procedure. In another configuration, the wedge 216, 316 angle or tube 416 angle may be such that a deployed position of sensors 112 corresponds with a specific distance from probe tip 106. The angle of wedges 216, 316 or tube 416 may be in the range of about 0° to about 90° to allow sensor deployment within the range of about 0° to about 90° from the probe tip 106 surface.

With reference to all of the preceding embodiments depicted in FIGS. 1-10, various arrangements of sensors 112 may be used in deployable assembly 114. In one embodiment, deployable assembly 114 may be positioned to record measurements at any point along or within the ablation zone 108 created by use of probe tip 106, including areas both along the longitudinal body 102 and radially outward therefrom.

In further embodiments, sensors 112 may be spaced at varied intervals along the length of deployable assembly 114. In some embodiments, such as where sensors 112 are temperature sensors, one arrangement may include four or five sensors 112 in each deployable assembly 114, each sensor spaced approximately 5 mm from the next sensor. A distal-most sensor 112 may be positioned at the distal end of the deployable assembly 114. In such an embodiment, when deployed as in FIG. 1, 5, 8, or 10, the proximal-most sensor 112 may be immediately adjacent the probe surface. The distal-most sensor 112 may be 1.5 to 2 cm total from the proximal-most sensor. This may result in a sensing diameter of a 3-4 cm zone of tissue. In another embodiment, which may also be applicable to temperature sensors, a first sensor 112 may be located at a distal end of deployable assembly 114. A second sensor 112 may be located approximately 2.5 mm proximal of the first sensor 112 along deployable assembly 114. A third sensor 112 may be located approximately 2.5 mm proximal of the second sensor 112 along deployable assembly 114. A fourth sensor 112 may be located approximately 5 mm proximal of the third sensor 112 along deployable assembly 114. A fifth sensor 112 may be located approximately 5 mm proximal of the fourth sensor 112 along deployable assembly 114, placing the fifth sensor approximately 1.5 cm proximal of the distal-most sensor 112. This configuration may provide higher resolution at the outer range of the ablation zone 108, where the thermal gradient 109 (FIG. 1) tends to be higher.

In a further embodiment, sensors 112 may be arranged as described in the preceding paragraphs, but may include the addition or substitution of one or more electrical conduction sensors for thermal sensors at any of the various points. For example, counting from the proximal end of deployable assembly 114, the second or third sensor 112 may be an electrical conduction sensor for either mono or bipolar electrical conduction recording for use during, e.g., cardiac ablation procedures.

It is noted that the foregoing embodiments are intended only to be illustrative, and do not constitute an exhaustive recitation of the possible combinations and arrangements of sensors 112. In the various embodiments, both those described above and those specific embodiments not described in the interest of brevity and clarity, the actual distance from the probe into ablation zone 108 of the sensors 112 would vary with the extent of deployment of the deployable assembly 114. For example, on a deployable assembly 114 including five sensors 112, each sensor 112 spaced 5 mm from each adjacent sensor 112, 100% deployment would result in a 2 cm radius (4 cm diameter) measurement zone, whereas a 50% deployment would result in a 1 cm radius (2 cm diameter) measurement zone.

Also provided herein is a method for performing targeted ablation of various tissues such as, e.g., the skin, esophagus, bladder, endometrium, breast, prostate, liver, heart, lung, pancreas, testis, uterus, muscle, bone, kidney, or other tissue, including temperature monitoring during ablation.

As shown in, e.g., FIGS. 4, 7, and 9, device 100 may initially be in a retracted, non-engaged position in which deployable assemblies 114 including sensors 112 are disposed within longitudinal body 102 of the probe. This positioning of the deployable assemblies 114 allows for their maintenance and secured positioning during insertion of probe tip 106 into the target tissue. Upon insertion of probe tip 106 into the target tissue, the deployable assemblies 114 may be deployed as shown in FIGS. 1, 5, 8, and 10, e.g., by control mechanism 118 on probe handle 104, from the longitudinal body 102 into the ablation zone 108 in the tissue. The sensors 112 are directed into the tissue at a precise angle from the probe surface via deflection wedges 216, 316 or deflection tubes 416 located at the distal end 105 of longitudinal body 102, just proximal of ablation zone 108 as described above.

In one embodiment, deployment of deployable assemblies 114 may occur prior to performance of an ablation procedure, in order to facilitate monitoring temperatures or other tissue characteristics once ablation is initiated, and in the case of cryoablation in particular, to avoid maneuvering through ice formation. In another embodiment, deployment occurs during or after ablation procedures. To accommodate desirable monitoring of temperature and other metrics, deployable assemblies 114 are capable of being positioned before, during, or after treatment. Deployment of the deployable assemblies 114 and sensors 112 into the tissue can be directed to any number of locations including, but not limited to, positions of predicted isotherms, to positions where the attainment of a specific temperature is desired, to positions where desired ablation is achieved, and into non-targeted tissue to assure minimal damage within that region. Following completion of the ablation procedure, deployable assemblies 114 may be retracted into longitudinal body 102 via use of control mechanism 118, and probe tip 106 can be removed from the tissue.

Though ablation device 100 has been described in terms of particular embodiments, the various embodiments and aspects of the invention may be utilized in various treatment procedures in a patient. The use of a thermal monitoring device benefits current ablative treatment procedures by utilizing a minimal invasive device and technique that achieves a more controlled ablation with greater precision, fewer procedures, and improved patient outcomes. It is noted that aspects of the invention may be varied to accommodate different sizes, shapes and dimensions of probes used in fields of medical devices. Aspects of the invention may also be integrated in fields outside the medical realm as desired. Such fields may include any temperature measurement or monitoring systems.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An ablation probe comprising:
a longitudinal body including a thermal ablation energy source, the longitudinal body having a proximal end and a distal end terminating at a probe tip;
a guide channel disposed on a radially outward facing surface of the longitudinal body;
at least one deployable assembly disposed within the guide channel, the deployable assembly including:
a deployment member, and
at least one sensor affixed to a distal end of the deployment member;
a control mechanism for controlling deployment in a distal direction and retraction in a proximal direction of the deployable assembly; and
a surface mounted deflection wedge on the distal end of the guide channel at an interface of the distal end of the longitudinal body and the probe tip,
wherein the surface mounted deflection wedge includes an angled face relative to the longitudinal body, the angled face extending distally and radially outwardly, wherein the angled face of the wedge is configured to guide the sensor to a specific target, and wherein the angled face guides the deployable assembly distally and radially outward as it is deployed.

2. The ablation probe of claim 1, wherein the thermal ablation energy source is one of a radio frequency (RF) energy, high intensity focused ultrasound (HiFU), thermoelectric resistive heat, helium gas, or a laser.

3. The ablation probe of claim 1, wherein the thermal ablation energy source is a cryosource, and wherein the cryosource is one of nitrogen, nitrous oxide, hydrogen, argon, propane, an alcohol, or carbon dioxide in one of a gas, liquid, critical, or supercritical state.

4. The ablation probe of claim 3, wherein the longitudinal body further comprises a supply tube for supplying the cryosource to the probe tip, and a return tube for returning the cryosource from the probe tip, wherein the return tube substantially concentrically surrounds the supply tube.

5. The ablation probe of claim 4, wherein the longitudinal body further comprises an outer probe sheath concentrically surrounding the return tube, and an insulative lumen disposed between the return tube and the outer probe sheath, concentrically surrounding the return tube.

6. The ablation probe of claim 1, wherein each of the at least one sensors is configured to sense one of: temperature, pressure, electrical impedance, electrical conduction, blood perfusion, thermal conductivity, thermal diffusivity, or sound propagation velocity.

7. The ablation probe of claim 6, wherein the at least one sensor comprises at least two sensors, wherein each sensor in the deployable assembly is axially spaced approximately 5 mm from the next sensor, and a distal-most sensor is axially spaced 1.5 to 2 cm from a proximal-most sensor.

8. The ablation probe of claim 1, further comprising a probe handle disposed at the proximal end of the longitudinal body, wherein the control mechanism is disposed on the probe handle.

9. The ablation probe of claim 1, wherein the at least one deployable assembly comprises two deployable assemblies.

10. The ablation probe of claim 1, wherein at least one sensor further comprises four or five sensors.

11. An ablation probe comprising:
a longitudinal body including a thermal ablation energy source, the longitudinal body having a proximal end and a distal end terminating at a probe tip;
a guide channel disposed adjacent to the longitudinal body;
a deflection wedge on an outer surface of the longitudinal body and at a distal end of the guide channel;
at least one deployable assembly disposed within the guide channel, the deployable assembly including:
a deployment member, and
at least one sensor affixed to a distal end of the deployment member; and
a control mechanism for controlling deployment in a distal direction and retraction in a proximal direction of the deployable assembly, wherein the thermal ablation energy source is a cryosource, wherein the cryosource is one of nitrogen, nitrous oxide, hydrogen, argon, propane, an alcohol, or carbon dioxide in one of a gas, liquid, critical, or supercritical state, wherein the longitudinal body further comprises a supply tube for supplying the cryosource to the probe tip, and a return tube for returning the cryosource from the probe tip, and wherein the return tube substantially concentrically surrounds the supply tube.

12. The ablation probe of claim 11, wherein the longitudinal body further comprises an outer probe sheath concentrically surrounding the return tube, and an insulative lumen disposed between the return tube and the outer probe sheath, concentrically surrounding the return tube.

* * * * *